US012178497B2

(12) United States Patent
Germain et al.

(10) Patent No.: US 12,178,497 B2
(45) Date of Patent: Dec. 31, 2024

(54) ARTHROSCOPIC DEVICES AND METHODS

(71) Applicant: Relign Corporation, Campbell, CA (US)

(72) Inventors: Aaron Germain, San Jose, CA (US); Jeff Norton, Emerald Hills, CA (US); Kyle Klein, San Jose, CA (US); Michael D Walker, San Francisco, CA (US)

(73) Assignee: Relign Corporation, Campbell, CA (US)

( * ) Notice: Subject to any disclaimer, the term of this patent is extended or adjusted under 35 U.S.C. 154(b) by 545 days.

(21) Appl. No.: 17/567,551

(22) Filed: Jan. 3, 2022

(65) Prior Publication Data
US 2022/0117650 A1 Apr. 21, 2022

Related U.S. Application Data

(63) Continuation of application No. 16/111,503, filed on Aug. 24, 2018, now Pat. No. 11,246,649.
(Continued)

(51) Int. Cl.
*A61B 18/14* (2006.01)
*A61B 17/00* (2006.01)
(Continued)

(52) U.S. Cl.
CPC ........ *A61B 18/148* (2013.01); *A61B 17/1604* (2013.01); *A61B 17/1606* (2013.01);
(Continued)

(58) Field of Classification Search
CPC .............. A61B 18/148; A61B 17/1604; A61B 17/1606; A61B 17/1615; A61B 17/32002;
(Continued)

(56) References Cited

U.S. PATENT DOCUMENTS 5,643,198 A 7/1997 Cucin
5,830,214 A 11/1998 Flom et al.
(Continued)

FOREIGN PATENT DOCUMENTS

CN 111629645 A 9/2020
EP 3675707 A1 7/2020
(Continued)

OTHER PUBLICATIONS

U.S. Appl. No. 16/111,503, filed Aug. 24, 2018, Arthroscopic Devices and Methods.
(Continued)

*Primary Examiner* — Ronald Hupczey, Jr.
*Assistant Examiner* — Abigail Bock
(74) *Attorney, Agent, or Firm* — SCHWEGMAN LUNDBERG & WOESSNER, P.A.

(57) ABSTRACT

A resecting probe includes a shaft assembly having an outer sleeve and an inner sleeve. The outer sleeve has an axial bore and an outer window in a distal side thereof, and the inner sleeve has an axial extraction channel and inner window in a distal side thereof. The inner sleeve is rotationally disposed in the axial bore of the outer sleeve to allow the inner sleeve window to be rotated in and out of alignment with the outer sleeve window, and the shaft assembly forms a flow aperture in a distal portion when the inner cutting window and the outer cutting window are out of alignment. An electrode is carried on the inner sleeve, and a motor drive is coupled to rotate the inner sleeve relative to the outer sleeve. A controller is coupled to the motor drive and controls rotation of the inner sleeve and can stop rotation of the inner sleeve in a stop position where the outer and inner windows are out of alignment, providing the flow aperture to allow cooling of fluid in a working space and cooling of the probe handpiece during use.

20 Claims, 14 Drawing Sheets

Related U.S. Application Data

(60) Provisional application No. 62/696,762, filed on Jul. 11, 2018, provisional application No. 62/551,150, filed on Aug. 28, 2017.

(51) Int. Cl.

| | | |
|---|---|---|
| *A61B 17/16* | (2006.01) | |
| *A61B 17/29* | (2006.01) | |
| *A61B 17/32* | (2006.01) | |
| *A61B 18/00* | (2006.01) | |
| *A61B 90/98* | (2016.01) | |

(52) U.S. Cl.
CPC .... *A61B 17/1615* (2013.01); *A61B 17/32002* (2013.01); *A61B 2017/00137* (2013.01); *A61B 2017/00477* (2013.01); *A61B 2017/00482* (2013.01); *A61B 2017/00876* (2013.01); *A61B 17/29* (2013.01); *A61B 2017/320024* (2013.01); *A61B 2017/320028* (2013.01); *A61B 2017/320032* (2013.01); *A61B 2018/00029* (2013.01); *A61B 2018/00083* (2013.01); *A61B 2018/00172* (2013.01); *A61B 2018/00196* (2013.01); *A61B 2018/00202* (2013.01); *A61B 2018/00208* (2013.01); *A61B 2018/00577* (2013.01); *A61B 2018/00589* (2013.01); *A61B 90/98* (2016.02); *A61B 2217/005* (2013.01); *A61B 2218/007* (2013.01)

(58) Field of Classification Search
CPC .................. A61B 90/98; A61B 17/29; A61B 2017/00137; A61B 2017/00477; A61B 2017/00482; A61B 2017/00876; A61B 2017/320024; A61B 2017/320032; A61B 2018/00029; A61B 2018/00083; A61B 2018/00172; A61B 2018/00196; A61B 2018/00202; A61B 2018/00577; A61B 2018/00589; A61B 2217/005; A61B 2218/007
See application file for complete search history.

(56) References Cited

U.S. PATENT DOCUMENTS

| | | |
|---|---|---|
| 6,610,059 B1 | 8/2003 | West, Jr. |
| 6,821,275 B2 | 11/2004 | Truckai et al. |
| 7,674,263 B2 | 3/2010 | Ryan |
| 8,333,763 B2 | 12/2012 | Truckai et al. |
| 9,155,555 B2 | 10/2015 | Obrien, II |
| 9,439,720 B2 | 9/2016 | Germain et al. |
| 9,681,913 B2 | 6/2017 | Orczy-timko et al. |
| 9,855,675 B1 | 1/2018 | Germain et al. |
| 10,022,140 B2 | 7/2018 | Germain et al. |
| 10,028,767 B2 | 7/2018 | Germain et al. |
| 10,052,149 B2 | 8/2018 | Germain et al. |
| 10,595,889 B2 | 3/2020 | Germain et al. |
| 11,246,649 B2 | 2/2022 | Germain et al. |
| 2002/0173776 A1 | 11/2002 | Batchelor et al. |
| 2003/0125639 A1 | 7/2003 | Fisher et al. |
| 2003/0163126 A1 | 8/2003 | West |
| 2006/0200123 A1 | 9/2006 | Ryan |
| 2008/0103439 A1 | 5/2008 | Torrance et al. |
| 2010/0106153 A1 | 4/2010 | West, Jr. |
| 2012/0191117 A1 | 7/2012 | Palmer et al. |
| 2013/0331833 A1 | 12/2013 | Bloom |
| 2014/0336643 A1 | 11/2014 | Orczy-timko et al. |
| 2016/0346036 A1 | 12/2016 | Orczy-Timko et al. |
| 2017/0224368 A1 | 8/2017 | Germain et al. |
| 2017/0258512 A1 | 9/2017 | Germain et al. |
| 2017/0258519 A1 | 9/2017 | Germain et al. |
| 2017/0303990 A1 | 10/2017 | Benamou et al. |
| 2018/0000534 A1 | 1/2018 | Germain et al. |
| 2018/0161088 A1 | 6/2018 | Poser et al. |
| 2018/0263649 A1 | 9/2018 | Germain et al. |
| 2019/0008538 A1 | 1/2019 | Germain et al. |
| 2019/0015151 A1 | 1/2019 | Germain et al. |
| 2019/0059983 A1 | 2/2019 | Germain et al. |
| 2019/0083121 A1 | 3/2019 | Benamou et al. |

FOREIGN PATENT DOCUMENTS

| | | |
|---|---|---|
| JP | 2020531201 A | 11/2020 |
| WO | WO-2016171963 A1 | 10/2016 |
| WO | WO-2017136414 A1 | 8/2017 |
| WO | WO-2019046131 A1 | 3/2019 |

OTHER PUBLICATIONS

"Japanese Application Serial No. 2020-512439, Notification of Reasons for Refusal mailed May 17, 2022", w/ English translation, 10 pgs.

"Japanese Application Serial No. 2020-512439, Response filed Jul. 25, 2022 to Notification of Reasons for Refusal mailed May 17, 2022", w/ English claims, 10 pgs.

"U.S. Appl. No. 16/111,503, Final Office Action mailed Jul. 20, 2021", 24 pgs.

"U.S. Appl. No. 16/111,503, Non Final Office Action mailed Feb. 19, 2021", 20 pgs.

"U.S. Appl. No. 16/111,503, Notice of Allowance mailed Oct. 6, 2021", 7 pgs.

"U.S. Appl. No. 16/111,503, Response filed May 13, 2021 to Non Final Office Action mailed Feb. 19, 2021", 14 pgs.

"U.S. Appl. No. 16/111,503, Response filed Sep. 20, 2021 to Final Office Action mailed Jul. 20, 2021", 11 pgs.

"Chinese Application Serial No. 201880070218.0, Notification to Make Rectification mailed May 14, 2020", (W/ English Translation), 2 pgs.

"Chinese Application Serial No. 201880070218.0, Response filed Jul. 29, 2020 to Notification to Make Rectification mailed May 14, 2020", 1 pg.

"European Application Serial No. 18851087.9, Extended European Search Report mailed Apr. 30, 2021", 7 pgs.

"European Application Serial No. 18851087.9, Response filed Nov. 29, 2021 to Extended European Search Report mailed Apr. 30, 2021", 25 pgs.

"International Application Serial No. PCT/US2018/048018, International Preliminary Report on Patentability mailed Mar. 12, 2020", 7 pgs.

"International Application Serial No. PCT/US2018/048018, International Search Report mailed Oct. 29, 2018", 2 pgs.

"International Application Serial No. PCT/US2018/048018, Written Opinion mailed Oct. 29, 2018", 5 pgs.

Allen-Bradley, "AC Braking Basics", Web article, Rockwell Automation, Rockwell International Corporation, [Online]. Retrieved from the Internet: <http://literature.rockwellautomation.com/idc/groups/literature/documents/wp/drives-wp004_-enp.pdf>, (Feb. 2001), 4 pgs.

Allen-Bradley, "What is Regeneration? Braking / Regeneration Manual: Regeneration Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.

ARTHROSCOPIC DEVICES AND METHODS

CROSS-REFERENCE TO RELATED APPLICATION

This application claims the benefit of provisional applications 62/551,150, filed Aug. 28, 2017, and 62/696,762, filed Jul. 11, 2018, the full disclosures of which are incorporated herein by reference.

BACKGROUND OF THE INVENTION

1. Field of the Invention

This invention relates to a medical system that includes variations of motor-driven arthroscopic shavers that carry RF electrodes for ablating of coagulating tissue.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems including, a reusable hand piece and a selection of interchangeable tool probes have different working ends have been proposed. Such working ends may each have two or more functionalities, such as soft tissue removal and hard tissue resection, so such tools systems can provide dozens of specific functionalities, providing great flexibility.

For example, such endoscopic tool systems may have tool probes which combine a rotatable cutter and a radiofrequency electrode suitable for ablation and/or coagulation. When operating in a cutting mode, a negative pressure is typically applied to the probe to draw tissue into a cutting window and thereafter suction tissue chips out through an extraction channel. When operating in an electrosurgical mode, in contrast, there typically would be no negative pressure applied and no fluid flow through the probe.

While the combination tool of the invention with both a rotatable cutter and an RF electrode provides a significant advantage, in some such designs, there is a need to cool the probe and/or hand piece when operating in the electrosurgical mode.

It is therefore an object of the present invention to provide improved surgical systems and methods for their use, such as improved arthroscopic tissue cutting and removal systems of the type which combine a rotatable mechanical cutter and a radiofrequency electrode suitable for ablation and/or coagulation. In particular, it would be advantageous to provide such a tissue cutting and removal system with a rotatable cutter and a radiofrequency electrode having an improved cooling function when operating in the electrosurgical mode. At least some of these objectives will be met by the inventions described herein.

2. Description of the Background Art

Relevant commonly owned patents and applications include U.S. Pat. Nos. 6,821,275; 8,333,763; 9,855,675; 9,681,913; and copending application Ser. Nos. 15/454,690; 15/483,940; 15/495,620; 15/633,372; 15/659,241; 15/271,187; 15/855,684; 15/920,130; 15/920,258; 15/974,565, the full disclosures of which are incorporated herein by reference.

SUMMARY OF THE INVENTION

The present invention provides improved apparatus and methods for resecting and otherwise treating tissue. Such apparatus and methods provide endoscopic tools for both mechanical resection and electrosurgical treatment, such as ablation and coagulation. The endosurgical tools also referred to as probes and resecting probes, will typically but not necessarily comprise a reusable handle and a removable or detachable probe shaft, where the probe shaft includes both a cutting function and an electrosurgical function. The probe shaft will be configured to allow for fluid aspiration during both cutting and electrosurgical operation, where the fluid flow provides cooling during the electrosurgical operation.

In a first aspect, the present invention provides a resecting probe comprising a shaft assembly and a motor drive. The shaft assembly includes (i) an outer sleeve having an axial bore and an outer window in a distal side thereof and (ii) an inner sleeve having an axial extraction channel configured to connect to a negative pressure source (typically for aspiration of tissue chips or debris as described further below) and an inner window in a distal side thereof. The inner sleeve is rotationally disposed in the axial bore of the outer sleeve which allows the inner sleeve window to rotate relative to the outer sleeve window to thereby cut tissue. The inner sleeve is typically motor-driven to cut tissue that is drawn into the windows and aspiration is applied to draw fluid and tissue debris through the extraction channel. The shaft assembly is further configured to form a flow aperture in a distal portion thereof when the inner cutting window and the outer cutting window are out of alignment, allowing a cooling fluid flow through the shaft assembled (and optionally a handpiece as described hereinafter) during electrosurgical use when the cutting windows are not aligned, blocking the tissue debris aspiration flow path. An electrode is carried on the inner sleeve, and the motor drive is coupled to rotate the inner sleeve relative to the outer sleeve.

The flow aperture can be formed in a variety of ways. For example, an outer sleeve aperture may be formed in a wall of the outer sleeve, wherein such outer sleeve aperture aligns with the inner window when the inner sleeve is in a stop position. Typically, the outer sleeve aperture comprises a plurality of slots formed in the wall of the outer sleeve, and fluid may flow into the extraction channel to provide a cooling function while tissue and other debris is blocked by the configuration of the slots. Alternatively, such apertures or slots may be formed in a wall of the inner sleeve, wherein such inner sleeve apertures align with the outer window when the inner sleeve is in the stop position. The inner sleeve apertures typically comprise a plurality of slots formed in the wall of the inner sleeve to serve a function similar to that described previously.

In preferred embodiments, a controller is coupled to the motor drive and configured to control rotation of the inner sleeve and to stop rotation of the inner sleeve in a stop position where the outer and inner windows are out of alignment, alternately called a window-closed position. The controller will typically be further configured to deliver energy to the electrode when the inner sleeve is in the stop position. The resecting probe will usually further comprise an aspiration source coupled to the extraction channel in the inner sleeve to draw tissue through the outer and inner windows when said windows are at least partially rotationally aligned, and the controller will often be further configured to operate in a first mode wherein both (i) the aspiration source draws fluid and tissue into said windows when at least partially aligned, and (ii) the motor drive rotates the inner sleeve to resect tissue. The controller may be further configured to operate in a second mode wherein (i) the aspiration source draws fluid through the flow aperture and inner window in said stop position, and (ii) the electrode is activated to apply energy to tissue.

Exemplary structural and operating parameters include adjusting the aspiration source to draw fluid through the flow-restricted aperture at a rate of at least 25 ml/min to enhance cooling of the probe and cooling of fluid in the working space. The flow apertures usually have dimensions selected to inhibit tissue from being aspirated therethrough, i.e., the apertures may act as a filter, typically comprising one or more elongated slots. The elongated slot typically has a width ranging from 0.005" to 0.10".

In other specific aspects of the resecting probe, the inner window is formed within a ceramic portion of the inner sleeve and the electrode is carried by a ceramic portion of the inner sleeve. A ceramic cutting tip may be carried at a distal end in the inner sleeve, and the electrode may be carried on a side of the ceramic cutting tip. In some instances, the ceramic cutting tip is fluted and the electrode is disposed between adjacent flutes.

In a second aspect, the present invention provides methods for treating tissue in a fluid-filled working space. Such methods comprise providing a probe including (i) an outer sleeve having an axial bore and an outer window in a distal side thereof and (ii) an inner sleeve configured to rotate in the axial bore of the outer sleeve and having an axial extraction channel and an inner window in a distal side thereof. The inner window is rotated in and out of alignment with the outer window as the inner sleeve rotates, and the sleeves are configured to form flow apertures in a distal portion thereof when the inner cutting window and the outer cutting window are out of alignment. A distal end of the probe is urged against a target tissue, and a negative pressure is applied through the extraction channel. The inner sleeve is rotated to resect tissue which is drawn through the outer window and the inner window when the windows are aligned as they rotate. The inner sleeve may be stopped in a stop position in which said outer and inner windows are not rotationally aligned, and an electrode carried by the inner sleeve may be activated, typically by applying radiofrequency (RF) current to treat tissue while actuating the aspiration source to draws fluid through the flow apertures to thereby cool the probe and fluid in the working space.

In particular examples, operating in a first mode comprise (i) controlling a motor drive to rotate the inner sleeve, and (ii) actuating an aspiration source to apply a negative pressure through the extraction channel. Typically, such a first mode includes operating the aspiration source to draw fluid through the windows at a rate of at least 25 ml/min. A second operating mode may comprise (i) stopping the inner sleeve in the stop position, (ii) actuating the aspiration source, and (iii) activating the electrode. In specific examples, operating the aspiration source draws fluid through the flow aperture at a rate of at least 25 ml/min.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable hand piece that carries a motor drive component. This description of the general principles of this invention is not meant to limit the inventive concepts in the appended claims.

Figure 1:
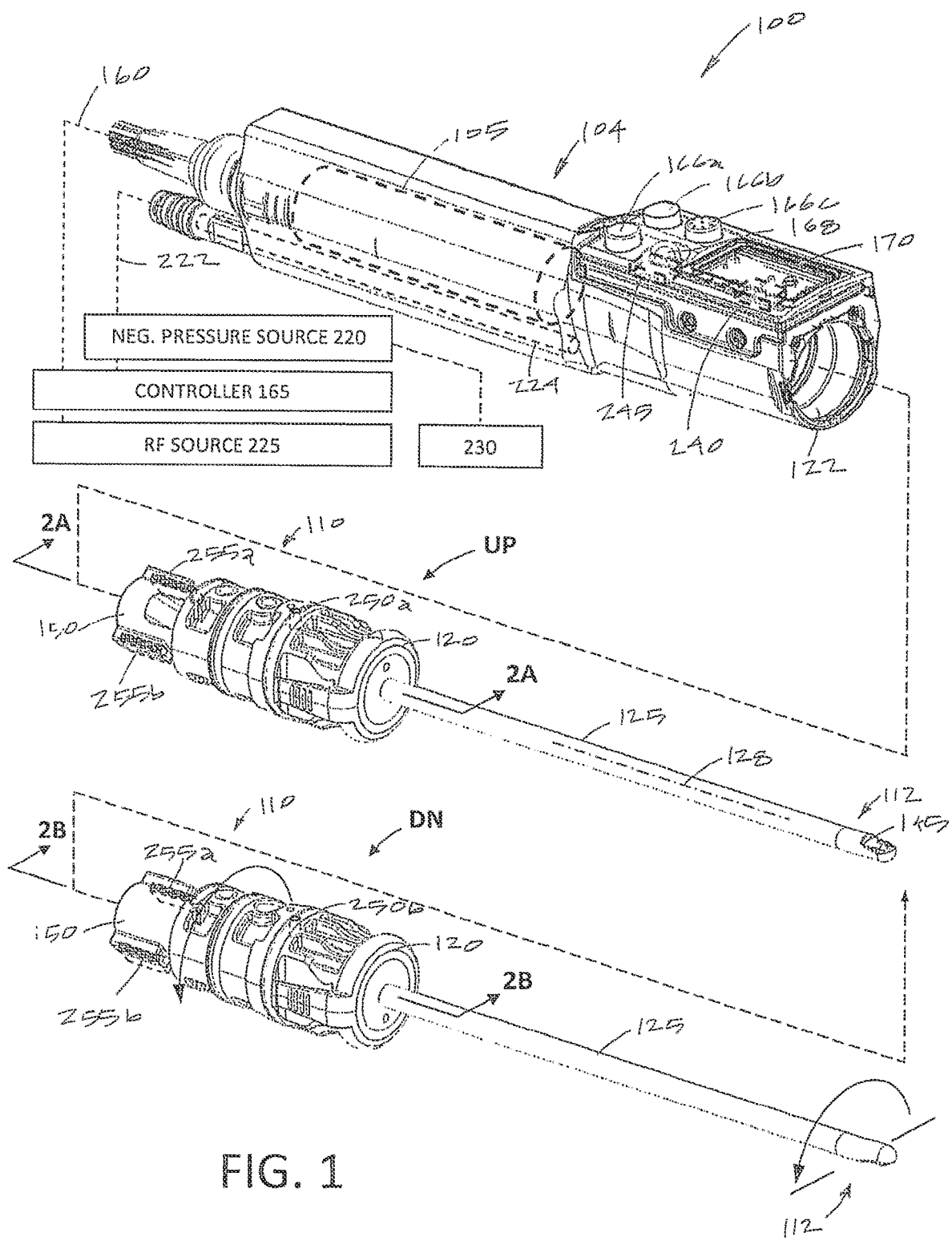
FIG. 1 is a perspective view of an arthroscopic cutting system that includes reusable hand piece with a motor drive and a detachable single-use cutting probe, wherein the cutting probe is shown in two orientations as it may be coupled to the hand piece with the probe and working end in upward orientation or a downward orientation relative to the hand piece, and wherein the hand piece includes an LCD screen for displaying operating parameters of system during use together with control actuators on the hand piece.

In one variation shown in FIG. 1, the arthroscopic system 100 of the present invention provides a hand piece 104 with motor drive 105 and a disposable shaver assembly or probe 110 with a proximal hub 120 that can be received by receiver or bore 122 in the hand piece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
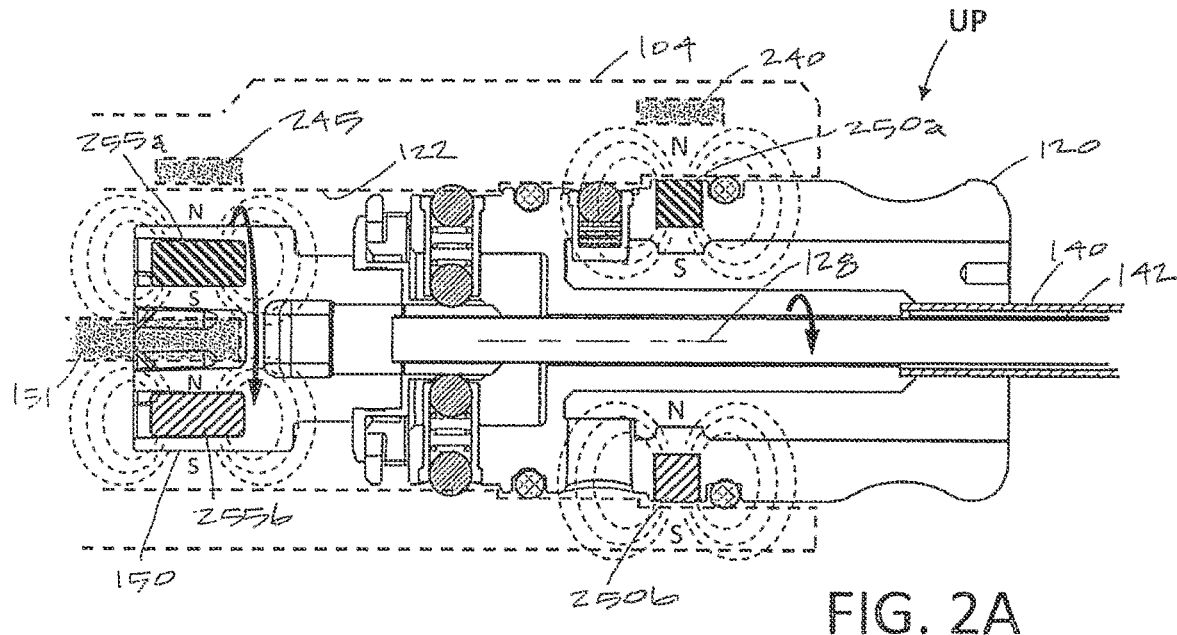
FIG. 2A is an enlarged longitudinal sectional view of the hub of the probe of FIG. 1 taken along line 2A-2A of FIG. 1 with the hub and probe in an upward orientation relative to the hand piece, further showing Hall effect sensors carried by the hand piece and a plurality of magnets carried by the probe hub for device identification, for probe orientation and determining the position of motor driven components of the probe relative to the hand piece.
Figure 3A:
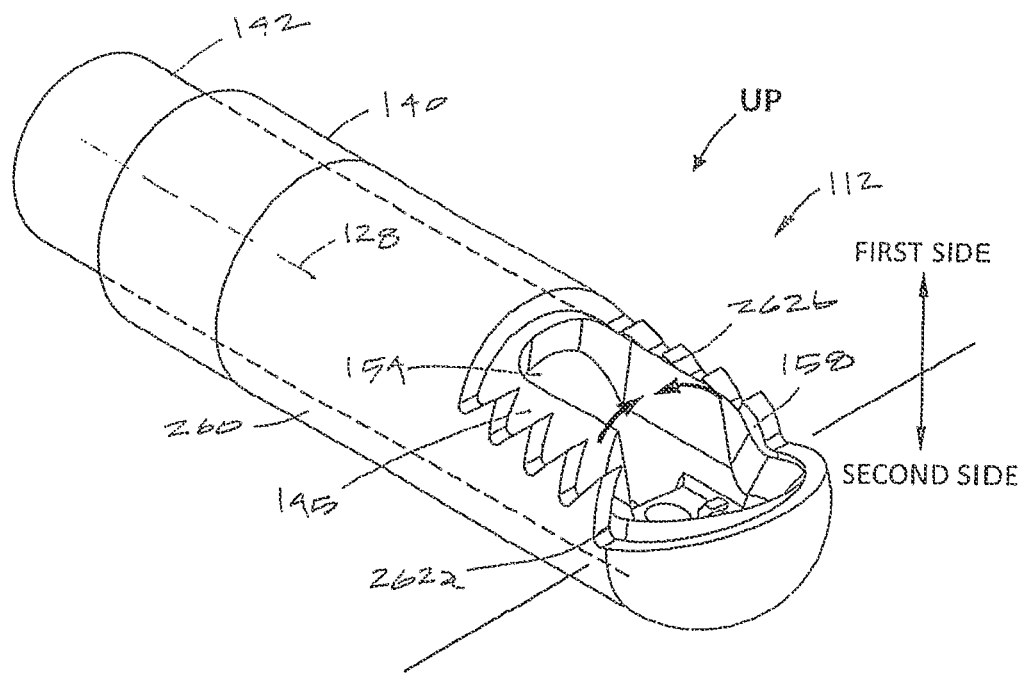
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
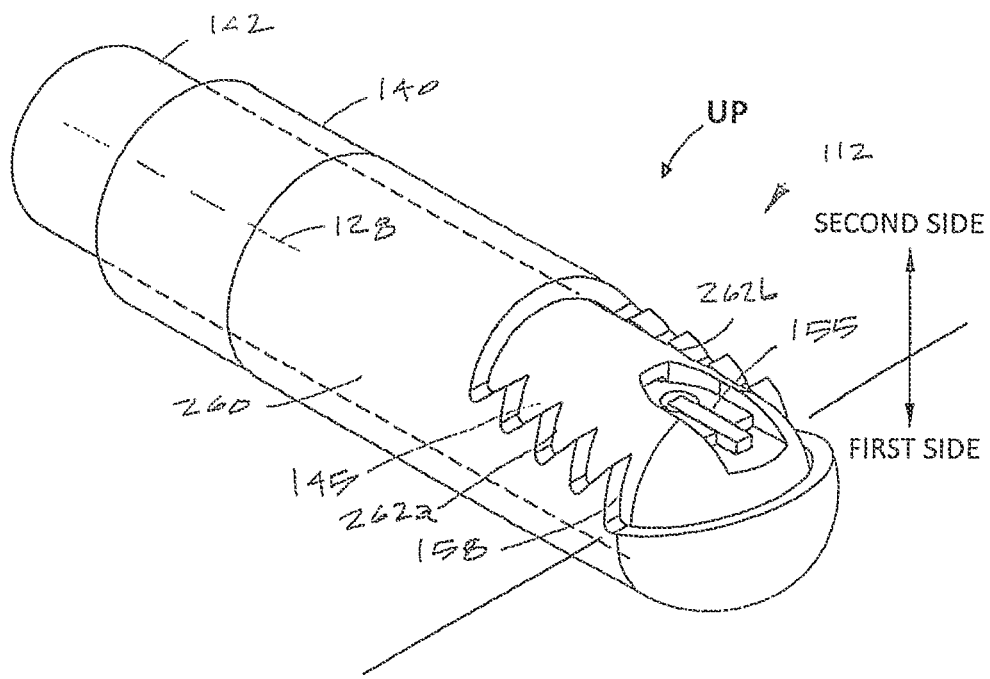
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the hand piece 104. More particularly, the hub 120 can be coupled to the hand piece 104 in an upward orientation indicated at UP and a downward orientation indicated at DN where the orientations are 180° opposed from one another. It can be understood that the upward and downward orientations are necessary to orient the working end 112 either upward or downward relative to the hand piece 104 to allow the physician to interface the cutting member 145 with targeted tissue in all directions without having to manipulate the hand piece in 360° to access tissue.

In FIG. 1, it can be seen that the handle 104 is operatively coupled by electrical cable 160 to a controller 165 which controls the motor drive unit 105 Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the hand piece for displaying operating parameters, such as cutting member RPM, mode of operation, etc.

Figure 4:
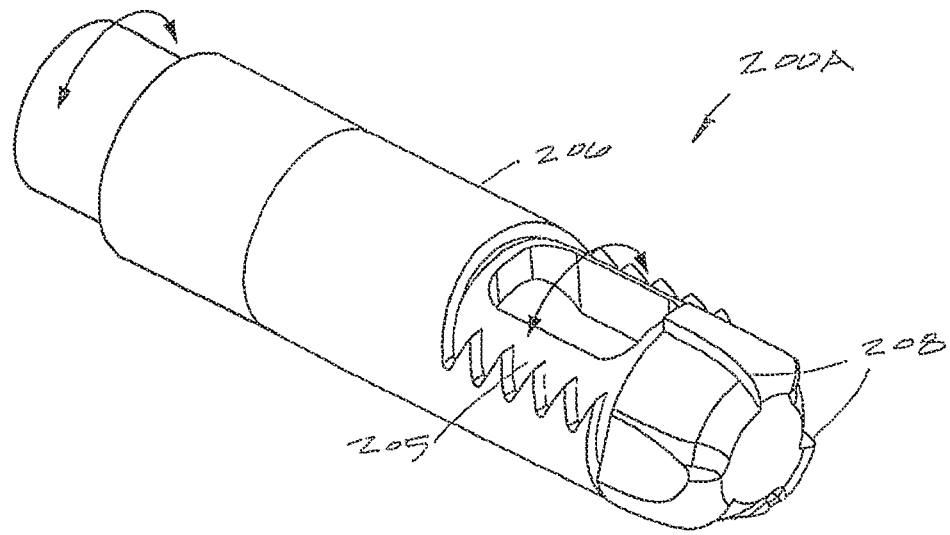
FIG. 4 is a perspective view of a working end of a variation of a probe that may be detachably coupled to the hand piece of FIG. 1, wherein the working end includes a bone burr extending distally from the outer sleeve.
Figure 5:
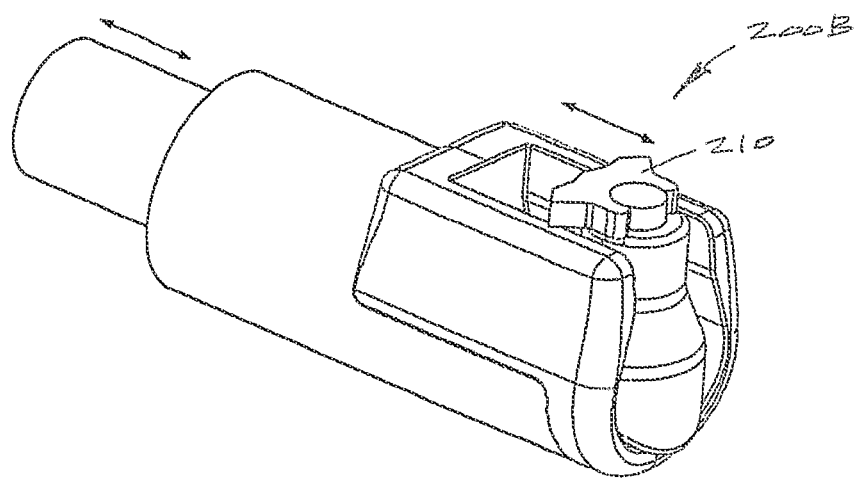
FIG. 5 is a perspective view of a working end of a variation of a probe that may be detachably coupled to the hand piece of FIG. 1, wherein the working end has a reciprocating electrode.
Figure 6:
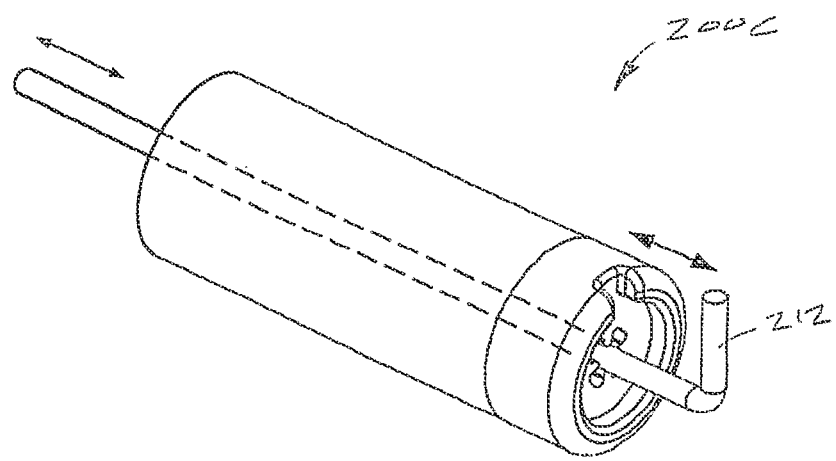
FIG. 6 is a perspective view of a working end of another variation of a probe that may be detachably coupled to the hand piece of FIG. 1, wherein the working end has a hook electrode that has extended and non-extended positions.
Figure 7:
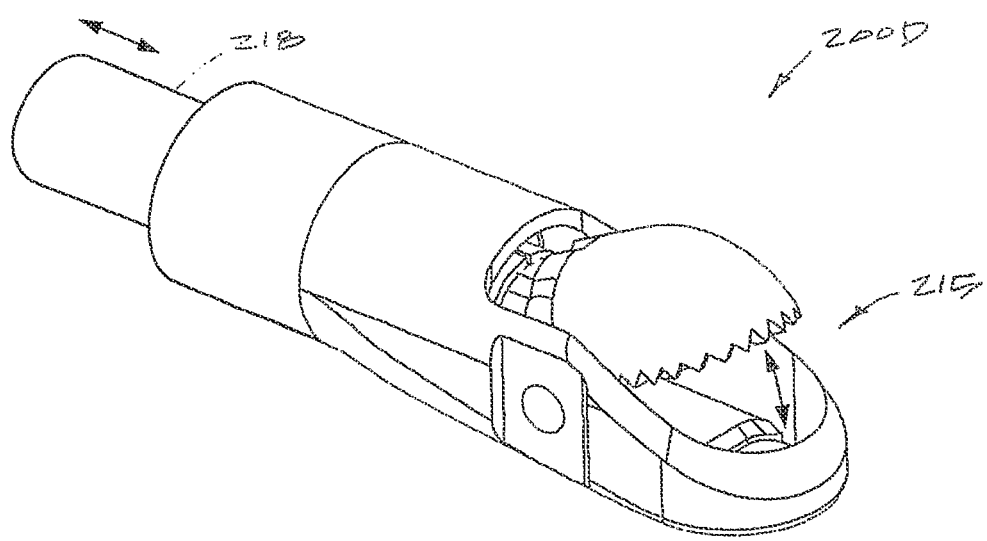
FIG. 7 is a perspective view of a working end of yet another variation of a probe that may be detachably coupled to the hand piece of FIG. 1, wherein the working end has an openable-closeable jaw structure for cutting tissue.

It can be understood from FIG. 1 that the system 100 and hand piece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same hand piece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in hand piece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and hand piece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to hand piece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the hand piece 104 in an upward or downward orientation relative to the hand piece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
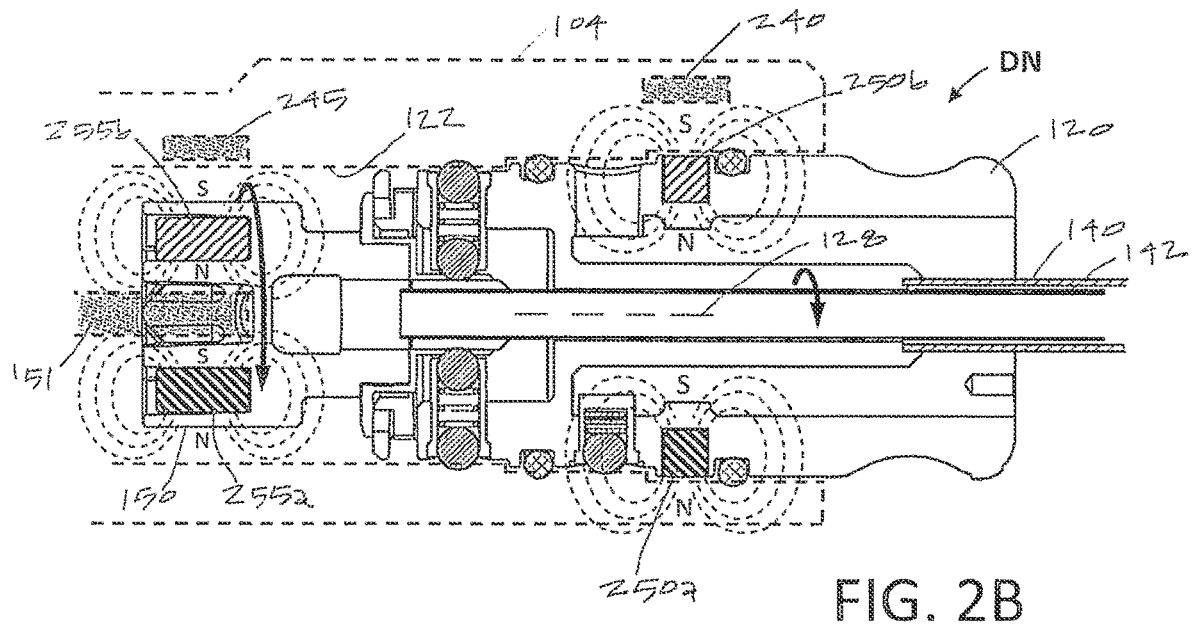
FIG. 2B is a sectional view of the hub of FIG. 1 taken along line 2B-2B of FIG. 1 with the hub and probe in a downward orientation relative to the hand piece showing the Hall effect sensor and magnets having a different orientation compared to that of FIG. 2A.

Referring to FIGS. 1 and 2A-2B, it can be seen that hand piece 104 carries a first Hall effect sensor 240 in a distal region of the hand piece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The hand piece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the hand piece, (ii) the upward or downward orientation of the probe hub 120 relative to the hand piece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in hand piece 104 is in axial alignment with either magnet 250a or 250b when the probe hub 120 is coupled to hand piece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a, 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to hand piece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the hand piece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on hand piece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
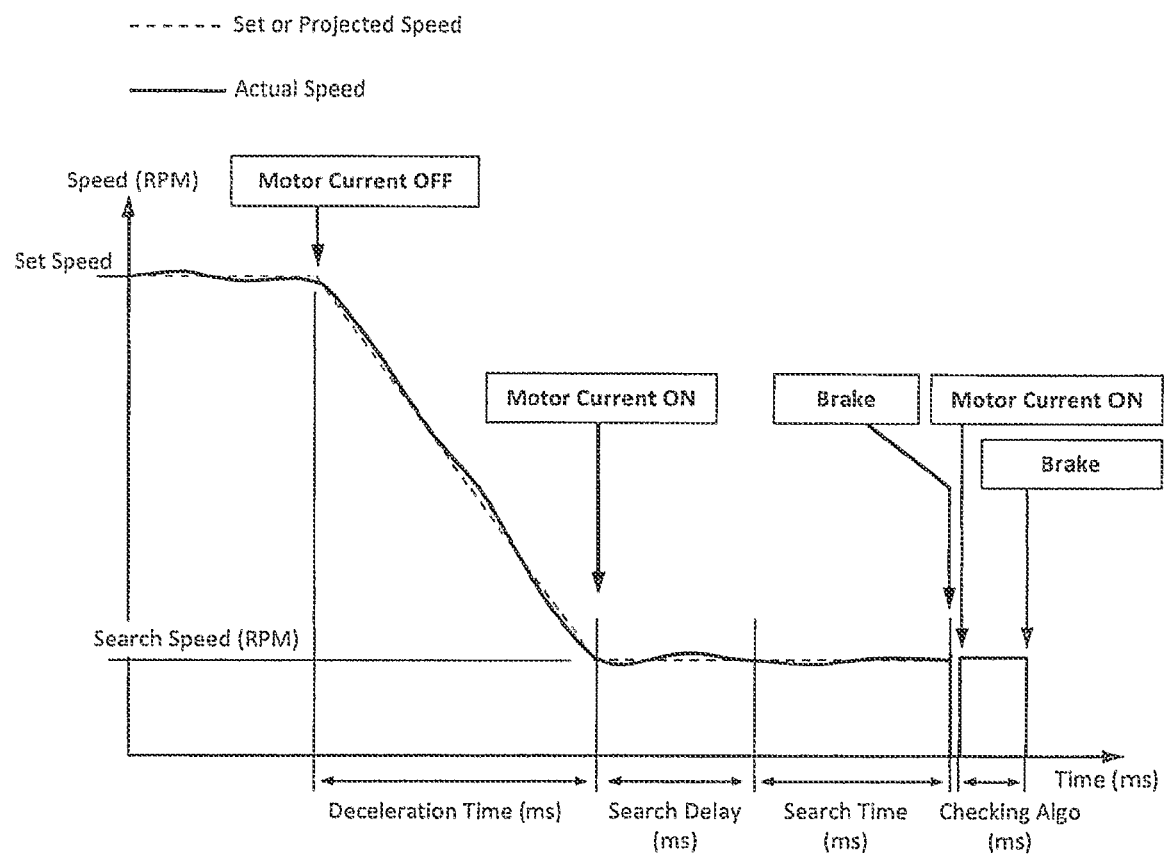
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p/pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the hand piece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a hand piece with a motor drive, a controller, and a probe with a proximal hub configured for detachable coupling to the hand piece, wherein the motor drive is configured to couple to a rotating drive coupling in the hub and wherein the drive coupling carries first and second magnets with North and South poles positioned differently relative to said axis, and coupling the hub to the hand piece, activating the motor drive to thereby rotate the drive coupling and magnets at least 180°, using a hand piece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
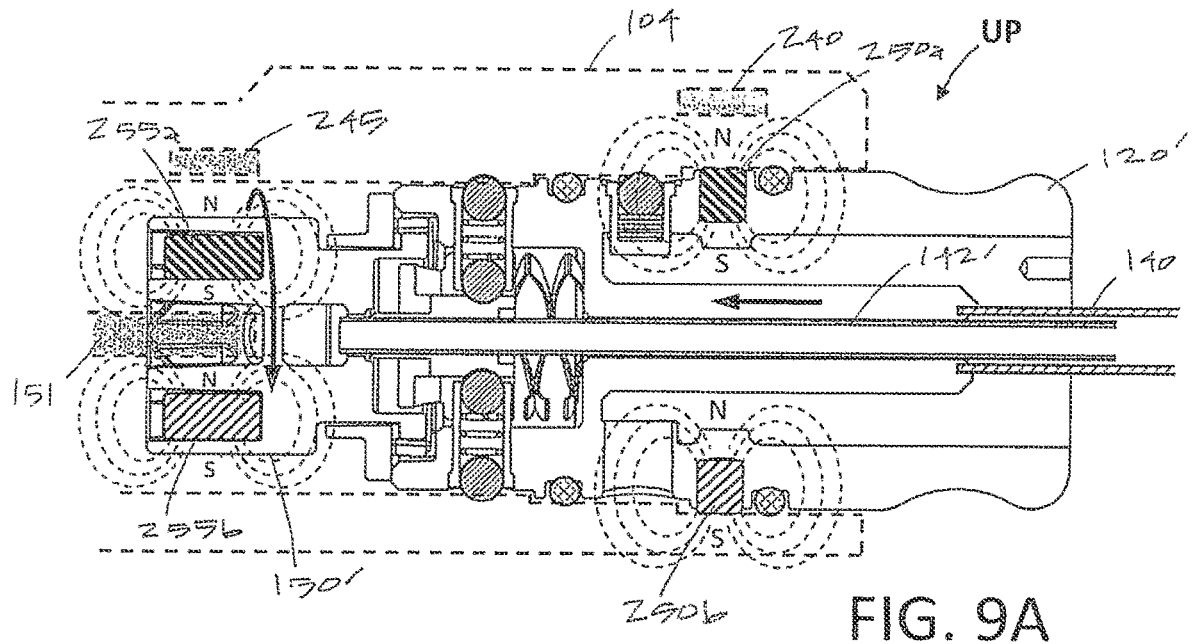
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the hand piece.
Figure 9B:
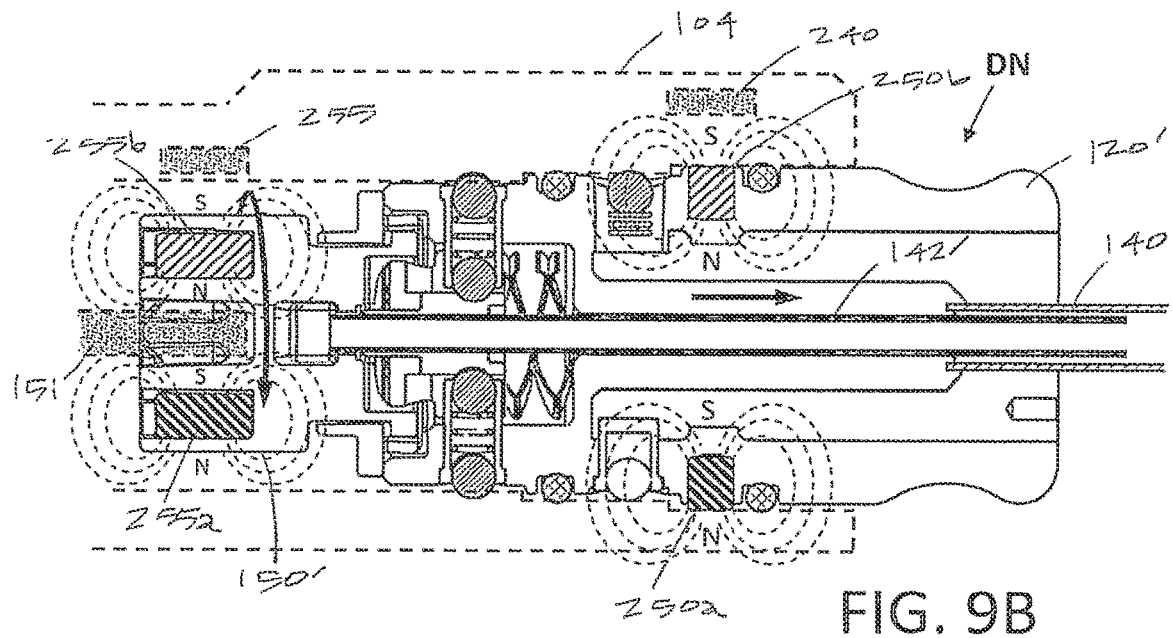
FIG. 9B is a sectional view of the hub of FIG. 9A rotated 180° in a downward facing position relative to the hand piece.

FIGS. 9A-9B are longitudinal sectional views of a probe hub 120' that corresponds to the working end 200B of FIG. 5 which has a reciprocating electrode 210. In FIGS. 9A-9B, the hand piece 104 and Hall affect sensors 240 and 245 are of course the same as described above as there is no change in the hand piece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Figure 10A:
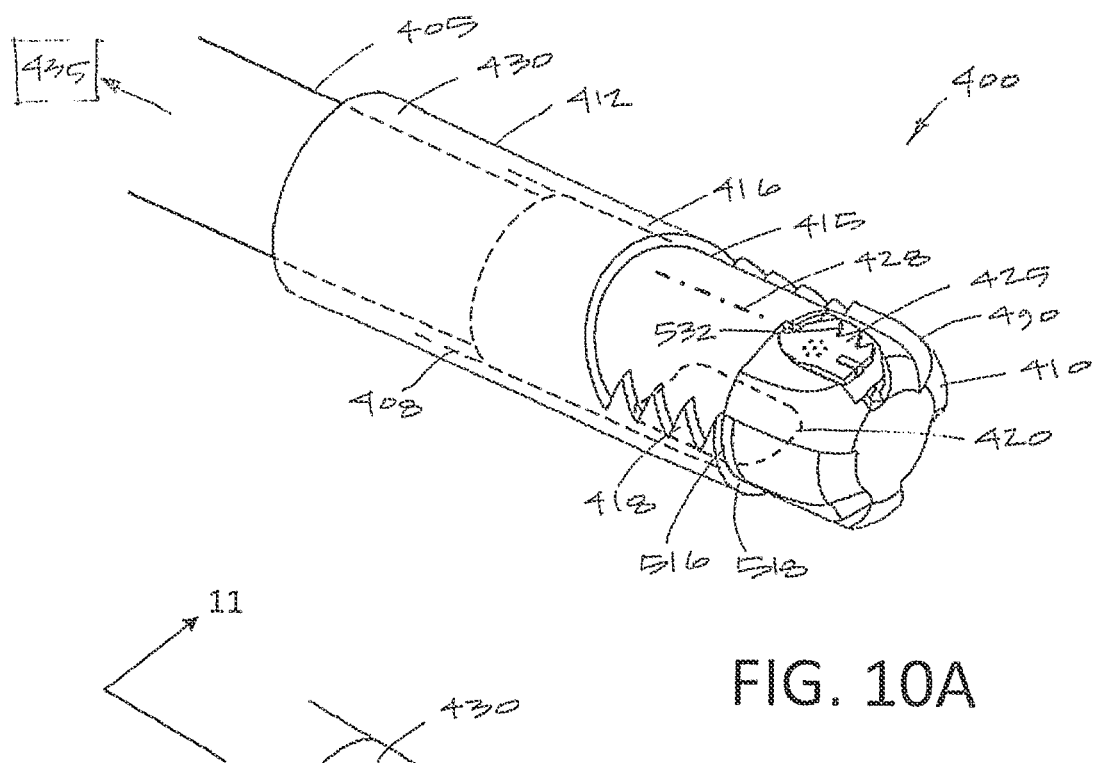
FIG. 10A is a perspective view of a working end of another variation of a probe that shows a motor-driven, rotating ceramic cutter carrying an electrode, with the cutter in a stopped position with the electrode aligned with the centerline of the window in the outer sleeve.
Figure 10B:
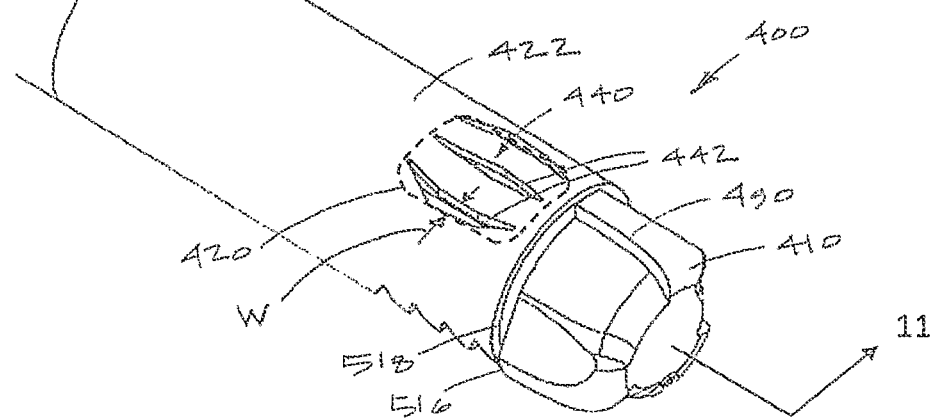
FIG. 10B is another view of the working end of FIG. 10A rotated 180° to show fluid outflow apertures in the outer sleeve
Figure 11:
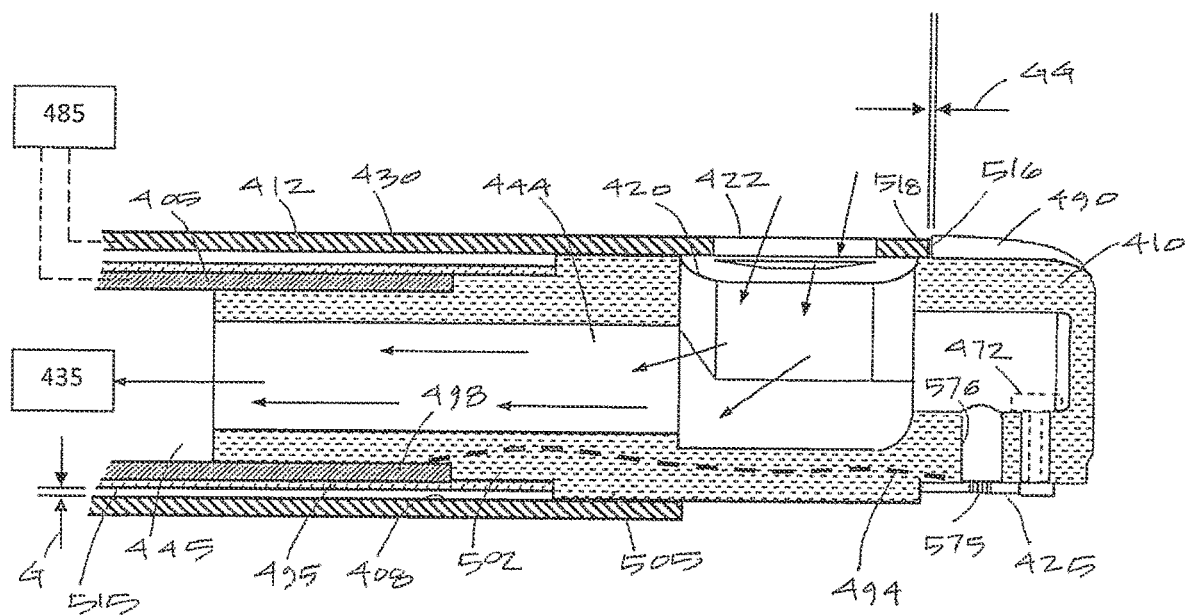
FIG. 11 is a sectional view of the working end of FIGS. 10A-109B taken along line 11-11 of FIG. 10B showing fluid outflows.

Now turning to FIGS. 10A-10B and 11, the working end 400 of another variation of the arthroscopic shaver is shown which is similar to that of FIGS. 1, 3A-3B and 4 which includes an inner sleeve 405 that carries a distal ceramic cutting body or cutter 410 adapted for rotation at high speeds in an axial bore 408 in a windowed metal outer sleeve 412. FIG. 10A shows the outer sleeve 412 in a rotational position in which the outer sleeve window 415 in a first side 416 of outer sleeve 412 is facing upwardly with teeth 418 along the edges of the window 415. The inner sleeve 405 and the ceramic cutter 410 are rotated to a position wherein a window 420 in the cutter 410 is facing downward and is not exposed in window 415 of the outer sleeve 412. FIG. 10B shows the entire working end 400 rotated 180° to a position wherein a second side 422 of the outer sleeve is facing upwardly. As described in previous embodiments, the rotating ceramic cutter 410 can be stopped in the position shown in both FIGS. 10A and 10B by a stop algorithm to thereby expose the active electrode 425 carried by the ceramic cutter 410 aligned generally with the centerline 428 of window 415 in the outer sleeve 412 as can be seen best in FIG. 10A. With the electrode 425 in the position shown in FIGS. 10A-10B, the physician can energize the active electrode 425 in connection with return electrode 430, which consists of a portion of outer sleeve 412 and ablate or coagulate tissue by translating the electrode 425 over a targeted tissue surface.

When using the electrode 425 to delivery energy to tissue, it can be easily understood that the saline distention fluid in the vicinity of energized electrode is heated by the energy delivery. It has been found that it is desirable to provide for a controlled fluid outflow through the working end 400 when the windows 415 and 420 of the respective outer sleeve 412 and inner sleeve or ceramic cutter 410 are not aligned as in FIGS. 10A-10B. Such a continuous fluid flow provided by the negative pressure source 435 will then extract heated distention fluid from the working space which can be important. Thus, as can be seen in FIG. 10B, at least one outflow aperture or flow aperture 440 is provided in the second side 422 of the outer sleeve 412. In a variation, referring to FIG. 10B, a plurality of elongated, narrow slots 442 are provided for such a fluid outflow.

FIG. 11 is a longitudinal sectional view of the working end 400 of FIG. 10B and shows the fluid flow through the slots 422 into central channel 444 of the ceramic cutter 410. In this variation, the slots are narrow and have a length that approximates that of window 420 in the ceramic cutter 410 through which the fluid flows into the central channel 444 and extraction channel 445 that extends through the probe (see FIG. 11). The width W of the slots 442 can range from 0.005" to 0.10" and the number of slots can range from 1 to 10 or more (FIG. 10B). It has been found that narrow slots are preferable over larger openings to allow such fluid outflows as the narrow slots prevent tissue debris from entering the slots. The total area of the slots for such outflows can be configured to provide a continuous flow in the range of 25 mL/min to 200 mL/min. In another variation, a plurality of round or oval apertures could be used instead of the elongated slots, wherein each such aperture has a cross-section ranging from 0.005" to 0.10". In another aspect of the invention, referring to FIG. 11, it can be seen that the cross-section of the outflow pathway increases from central channel 444 in the ceramic cutter 410 to the larger extraction channel 445 in the inner sleeve 405 which communicates with the negative pressure source. Such an increase in cross section of the fluid outflow pathway in the proximal direction assists in preventing clogs as any extracted tissue or bone chips are more effectively floating and entrained in the fluid outflow.

Figure 12A:
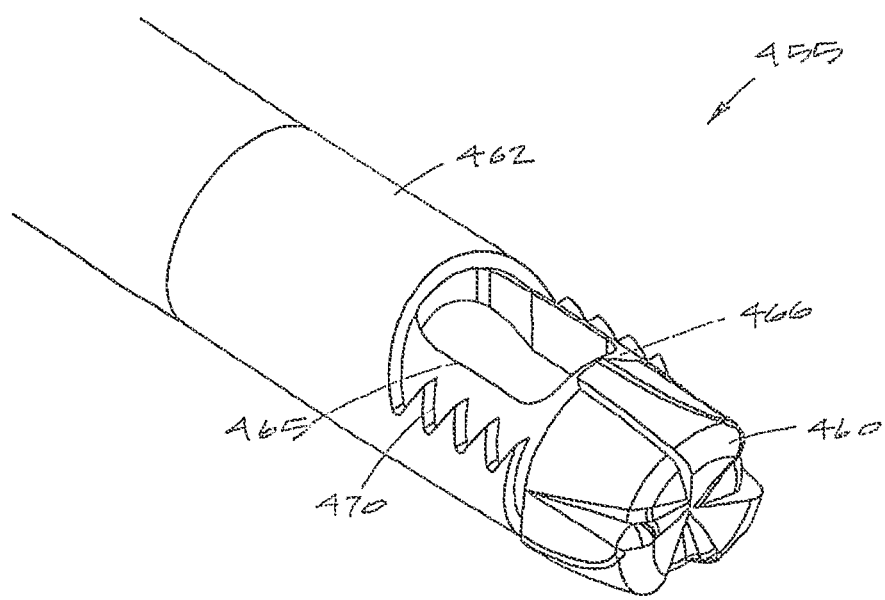
FIG. 12A is a perspective view of a working end of another variation of a probe that shows a motor-driven, rotating ceramic cutter carrying an electrode.
Figure 12B:
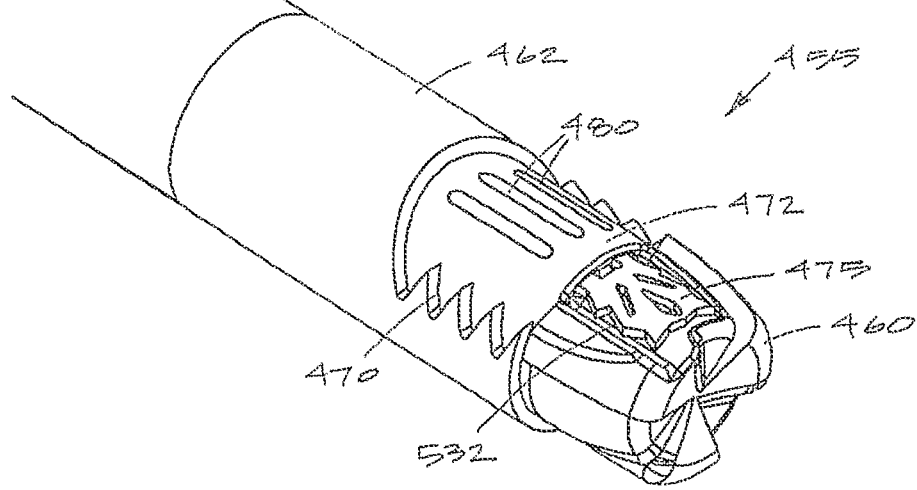
FIG. 12B is another view of the working end of FIG. 12A with the ceramic cutter rotated 180° to show fluid outflow apertures in the ceramic cutter.

Now turning to FIGS. 12A-12B, the working end 455 of another variation of the arthroscopic shaver is shown which is similar to that of FIGS. 10A-10B. The ceramic cutting body or cutter 460 that rotates in the metal outer sleeve 462. FIG. 11A shows the ceramic cutter in a rotational position in which the window 465 in a first side 466 of the cutter 460 is aligned with the window 470 in the outer sleeve 462. FIG. 11B shows the ceramic cutter 460 rotated 180° to a position wherein a second side 472 of the ceramic cutter 460 is exposed in the window 470 of the outer sleeve 462. As described previously, the ceramic cutter 460 can be stopped in the position shown in FIG. 11B by the controller's stop algorithm to thereby expose an active electrode 475. The physician then can energize the active electrode 475 to ablate or coagulate tissue. In this variation, the second side 472 of the ceramic cutter 460 is configured with at least one elongated slot 480 which are configured to allow fluid flow through the slots 480. Thus, this configuration provides fluid flows through the working end 455 to cool a distention fluid in the working space similar to that of the working end of FIGS. 10A-10B, except the slots or slots 480 are in the ceramic cutter 460 instead of the outer sleeve.

In general, a resecting probe for operating in a fluid-filled working space is provided which comprises a shaft assembly including (i) an outer sleeve having an outer window in a distal first surface and a flow aperture in a second surface that is opposed to the first surface; and (ii) an inner sleeve with a inner cutting window rotationally disposed in a bore of the outer sleeve, an aspiration source coupled to a lumen in the inner sleeve adapted to draw tissue into the outer and inner windows when said windows are at least partially rotationally aligned, a motor drive for rotating the inner sleeve and a controller configured for stopping rotation of the inner sleeve in a stop position in which said outer and inner windows are not rotationally aligned, and an electrode carried by a distal end of the inner sleeve configured for delivering energy to tissue when the inner sleeve is in said stop position. Such a tissue resecting probe further includes a controller that is adapted to operate in a first mode in which (i) the aspiration source draws fluid and tissue into said windows when at least partially aligned, and (ii) the motor drive rotates the inner sleeve to resect tissue. Further, such a tissue resecting probe has a controller adapted to operate in a second mode in which (i) the aspiration source draws fluid through the flow aperture and inner window in said stop position, and (ii) the electrode is activated to apply energy to tissue.

A method corresponding to the invention comprises providing a probe with an elongated shaft assembly including (i) an outer sleeve having an outer window in a distal first surface and a flow aperture in a second surface that is opposed to the first surface, and (ii) an inner sleeve with an inner window rotationally disposed in a bore of the outer sleeve, rotating the inner sleeve to thereby resect tissue while actuating an aspiration source coupled to a lumen in the inner sleeve, stopping the inner sleeve in a stop position in which said outer and inner windows are not rotationally aligned and activating an electrode carried by the inner sleeve to treat tissue while actuating the aspiration source to draws fluid through the flow aperture to thereby cool the probe.

In this method, a controller operates in a first mode to (i) control a motor drive to rotate the inner sleeve and (ii) actuate the aspiration source. Thereafter, the controller operates in a second mode to (i) stop the inner sleeve in the stop position, (ii) actuate the aspiration source, and (iii) energize the electrode to ablate or cauterize tissue.

Now turning back to FIG. 11, another aspect of the invention relating to the working end 400 and ceramic cutter 410 is shown. As previously described, the inner sleeve 405 and ceramic cutter 410 are adapted to rotate in bore 408 of the outer sleeve 412. The distal region of the ceramic cutter 410 includes burr edges 490 which are configured for cutting bone. For such bone cutting, the motor drive is adapted to rotate the ceramic cutter 410 at very high speeds, for example from 10,000 to 20,000 RPM. As can be seen in FIG. 11, the inner sleeve 405 is electrically conductive and functions to carry RF current from RF source 485 to the active electrode 425 by electrical lead 494 indicated schematically in FIG. 11. As described previously, still referring to FIG. 11, the outer sleeve 412 functions as a return electrode 430. For this reason, the inner sleeve 405 is covered with an insulator layer 495 which can be an insulative heat shrink polymer, for example, FEP, PTFE or the like. The inner sleeve assembly which includes inner sleeve 405 and ceramic cutter 410 as shown in FIG. 11 includes several features that insure durability and electrosurgical functionality. In one aspect, the insulator layer 495 is adapted to cover the distal end 498 of the inner sleeve 405 and overlap a portion 502 of the ceramic cutter 410. Such an overlap is at least 0.10" and preferably greater than 0.20" and is important to insure that there is no possibility of electrical shorting between the inner sleeve 405 and outer sleeve 412 which are immersed in a saline environment. In a second aspect, the ceramic cutter 410 has a body surface 505 with an outer diameter that is dimensioned for a snug rotating fit in bore 408 of the outer sleeve 412. Further, it can be seen that a gap indicated at G is provided between the outer surface 515 of the insulator layer 495 and the bore 408 of outer sleeve 412. It can be understood that under high rotational speeds, it is necessary to insure that the outer surface 515 of insulator 495 does not contact the outer sleeve 412 which would cause immediate wear on the polymer insulator layer 495. Thus, the only bearing surface of the inner sleeve assembly comprises the outer body surface 505 of the ceramic cutter 410 which rotates in the bore 408 of outer sleeve 412. The gap G is at least 0.005" and often greater than 0.010".

In another aspect of the invention, as can be seen in FIGS. 10A and 11, the proximal faces 516 of the burr edges 490 closely interface with the distal end 518 of the outer sleeve 412. The inner sleeve assembly (inner sleeve 405 and ceramic cutter 410) are coupled to a proximal hub assembly (not shown) which is configured to maintain the ceramic cutter 410 in an axial position without tolerance between the proximal faces 516 of burr edges 490 and the distal end 518 of outer sleeve 412. In a variation, the gap indicated GG is less than 0.005" or less than 0.002" (FIG. 11). Such tight tolerances prevents unwanted stress on both the ceramic cutter 410 and outer sleeve 412 when the physician may apply substantial sideways pressure on the working end 400 and ceramic member 410 when cutting bone.

In another aspect of the invention shown in FIGS. 10A and 12B, the electrodes 425 and 475 are configured with a plurality of sharp edges 532 that allow for more effective RF current flow from the electrode to tissue. In another aspect, the electrode 425 has a substantial surface area, and in a variation, the electrode has a surface area of at least 5 mm$^2$ or at least 10 mm$^2$.

Figure 13:
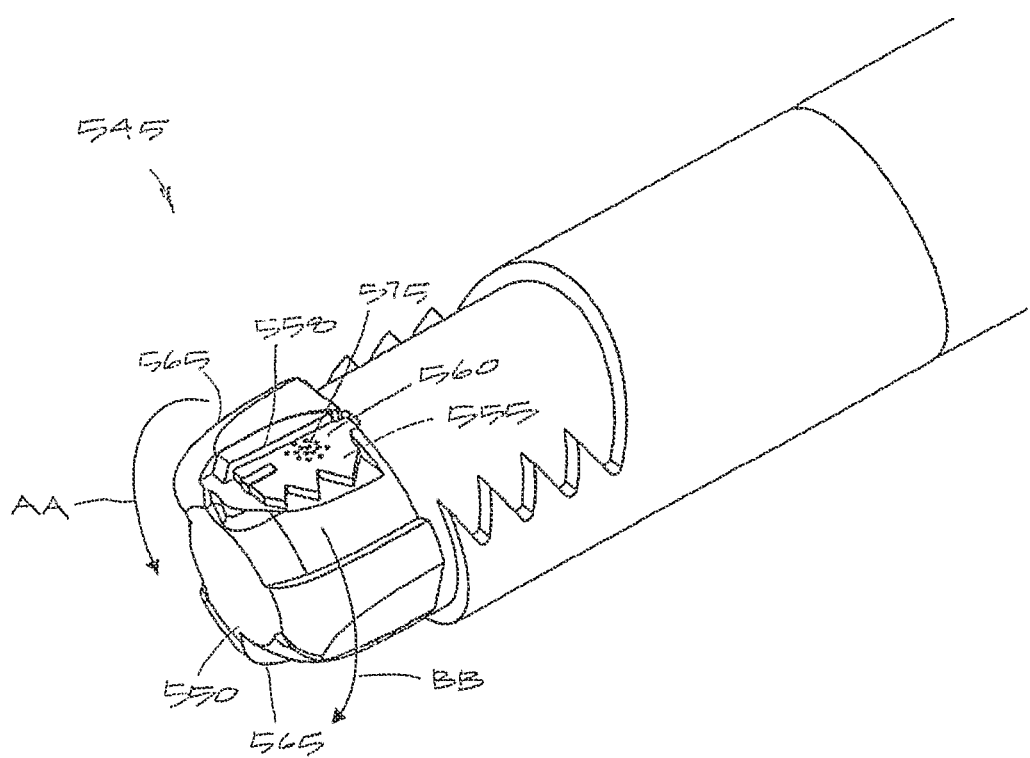
FIG. 13 is a perspective view of a working end of another variation of a probe that shows a motor-driven, rotating ceramic cutter carrying an electrode, wherein the electrode has a radial edge extending radially outward that is adapted for engaging tissue while being rotated and energized.

FIG. 13 shows another probe working end 545 that illustrates another aspect of the invention. In FIG. 13, the ceramic cutter 550 carries electrode 555 which is similar to the electrodes shown in FIGS. 10A and 12B, except the electrode 555 includes an additional feature which comprises a radial edge 558 that extends outwardly from the flat surface 560 of the electrode 555. The radial edge 558 extends upward to the height of the burr edge 565. As can be understood from FIG. 13, when the ceramic cutter 550 rotates in the direction of arrow AA, the burr edges 565 will cut bone. When the cutter 550 is rotated in this direction (arrow AA), the radial edge 558 of electrode 555 will be on the trailing edge of the burr and will not interfere with bone cutting. However, when the physician actuates the controller to operate the motor drive to rotate the ceramic cutter 555 in the direction of arrow BB, the radial edge 558 of electrode 555 will engage tissue as it rotates since the edge extends radially outward from the flat surface 560 the electrode 555. While the active electrode 555 has been described previously being used in a stationary position to ablate or coagulate tissue, it has been found that it is also useful to rotate the energized electrode 525 in direction BB. When rotating the energized electrode 555, the radial edge 558 of electrode 555 can then simultaneously cut and ablate or coagulate tissue. In other words, the radial edge 558 of the electrode 555 then uses both mechanical and electrosurgical energy to remove and ablate or coagulate tissue contemporaneously.

Referring back to FIG. 11, it can be seen that the electrode 425 is secured to the ceramic cutter 410 by a rivet 572 shown in phantom view. FIG. 11 further shows micropores 575 in the electrode 425 that communicate with passageway 576 in the ceramic cutter 410 which in turn communicates with the interior channel 444 in the cutter 410 and negative pressure source 435 which can reduce bubbles around the electrode surface when using the energized electrode 425.

Figure 15A:
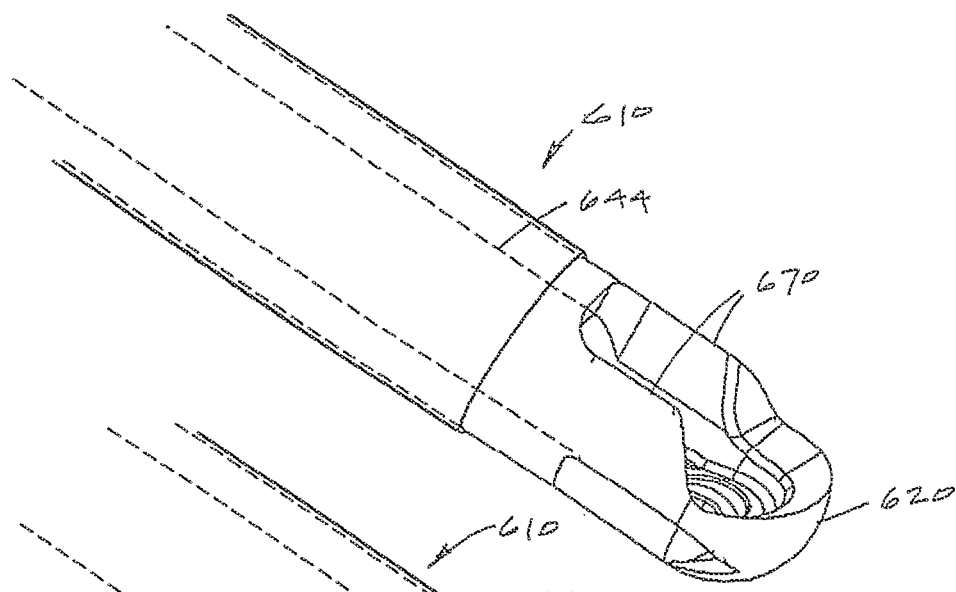
FIG. 15A is view of the working end of the inner sleeve and ceramic cutting member removed from the outer sleeve in a first rotational orientation.
Figure 15B:
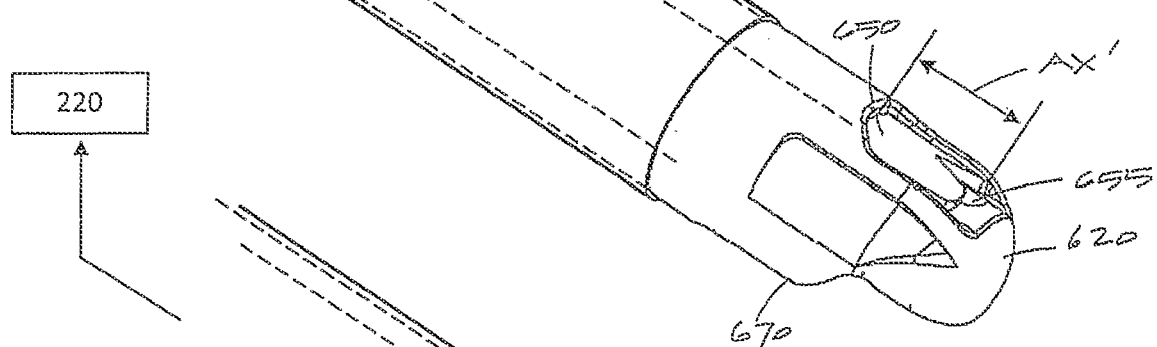
FIG. 15B is view of the inner sleeve and ceramic cutting member of FIG. 15A in a second rotational orientation that is rotated 180° from the view of FIG. 15A.
Figure 14:
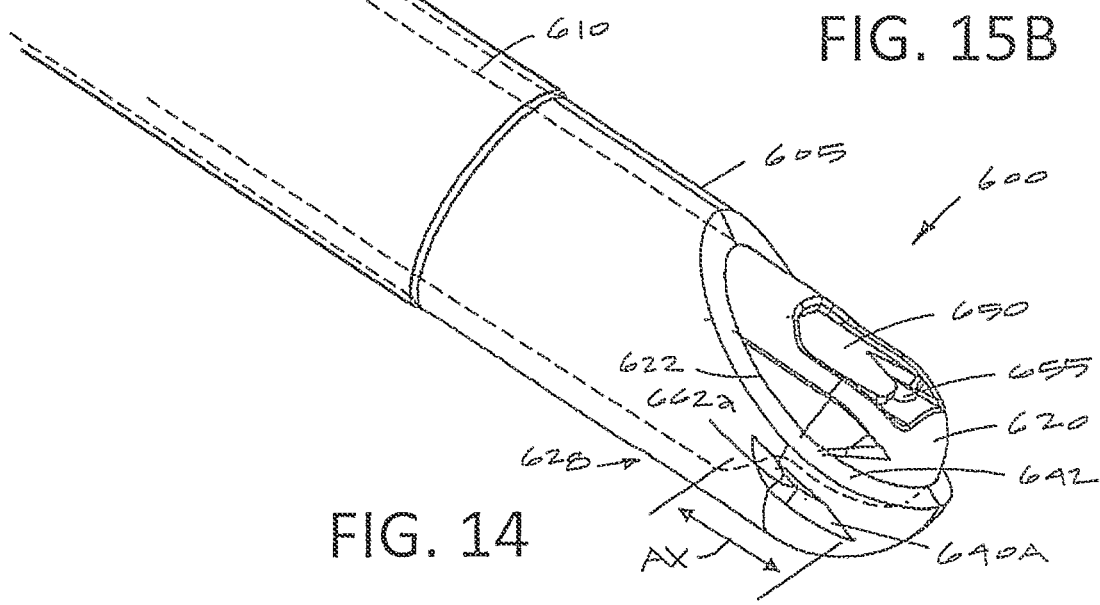
FIG. 14 is a perspective view of a another variation of a working end of a single-use probe similar to that of FIGS. 3A-3B with an inner sleeve and ceramic cutting member that carries an active RF electrode that rotates in an outer sleeve, wherein the outer sleeve can be metal or ceramic.

Now turning to FIG. 14, another variation of an arthroscopic probe is shown that is similar to that of FIGS. 3A-3B in which the RF probe working end 600 again includes a windowed outer sleeve 605 and a rotatable inner sleeve 610 (see FIGS. 15A-15B) that carries a ceramic cutting member 620 that rotates in the window 622 of the outer sleeve. In this variation, outer sleeve 605 is shown be fabricated of a metal such as stainless steel, however, the outer sleeve 605 and distal end thereof could also be a ceramic. As can be seen in FIG. 14, the distal end portion 628 of outer sleeve 605 includes side apertures or flow apertures 640A and 640B adjacent the window 622 that perform functions as described previously, including cooling the fluid in the working space and cooling the handpiece with continuous fluid flow through the extraction channel.

It should be appreciated that a number of such side apertures in this variation can number from 2 to 20 or more and are spaced apart from window edges 642 such that when the inner sleeve 610 is in the window-closed or non-aligned position as shown in FIG. 14, the apertures 640A and 640B communicate fully with the interior passageway 644 within ceramic cutting member 620 and inner sleeve 610 such that aspiration from a negative pressure or aspiration source 220 (FIG. 1) will pull saline through the apertures 640A and 640B.

As described previously, the inner sleeve 610 can be stopped in the position shown in FIG. 14 with the electrode 650 fully exposed in window 622. Thereafter the electrode 650 can be energized and used for ablating or coagulating tissue. In such a method of use, the energized electrode 650 can heat the saline solution in a working space which is undesirable. In this variation, an opening or aperture 655 adjacent and beneath the electrode 650 is adapted to provide fluid outflows therethrough. However, the volume of fluid aspirated through aperture 655 is limited. In such a method of use, the fluid outflow passes through the passageway 644 in the inner sleeve 610 and also the flow channel 224 in hand piece 104 (see FIG. 1). After a period of continuous use, the energized electrode 650 can cause unwanted heating of the handle 104 due to an extended period of time in which such heated fluid flows through the probe shaft and handle 104 (FIG. 2).

Figure 16:
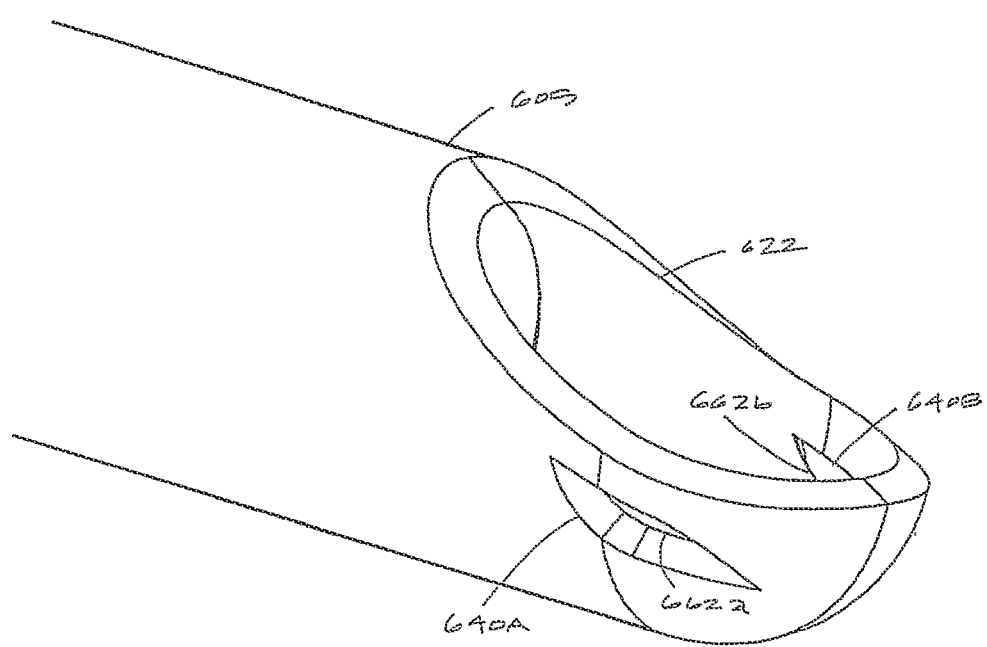
FIG. 16 is view of the outer sleeve of FIG. 14 separated from the inner sleeve to show the side or cooling apertures.

In the variation shown in FIG. 16, the negative pressure source 220 (FIG. 1) can aspirate substantially larger volumes of fluid through the apertures 640A and 640B which is advantageous for multiple reasons. In one aspect, the flows through the side apertures 640A, 640B can reduce outflows through the aperture 655 which then reduces the chance of fluid flow through aperture 655 from extinguishing plasma that is ignited about the electrode 650 in a tissue ablation mode. In a second aspect, increased fluid outflows through the side or cooling apertures 640A, 640B can substantially reduce the temperature of fluid in the working space of the joint due to increased fluid inflows into and through the working space. In a third aspect, the continuous outflow through the side apertures 640A, 640B allows the controller algorithm to continuously modulate inflows to match the outflows thus maintaining expansion of the joint cavity. In other words, the continuous inflows and outflows prevent collapse of the joint cavity which often occurs with commercially available probes which start and stop the inflow and outflow pumps based on pressure calculations which result in lag in response time. In a fourth aspect, it has been found that the temperature of handpiece 104 (FIG. 1) can be cooled significantly, for example, by 10° C. or more when energizing the electrode 650 continuously for one minute, which is a reasonable standard for comparing handle temperatures with a previous embodiments without the side apertures. In one variation, the fluid outflow through the side apertures 640A-640B is at least 25 ml/min, at least 50 ml/min, at least 100 ml/min, at least 150 ml/min or at least 200 ml/min. In contrast, the fluid outflow through the aperture 655 adjacent the electrode 650 is between 5 ml/min and 100 ml/min and more typically between 10 ml/min and 50 ml/min.

FIG. 16 shows the outer sleeve 605 FIG. 14 with the inner sleeve 610 and cutting ceramic cutting member 620 removed where it can be seen that the axial length AX of the apertures 640A and 640B is similar to, or at least 80% of, the axial length AX' of the electrode 650. Further, the inner edges 662a and 662b of the apertures 640A and 640B are sharp which provides additional functionality (FIG. 16). It can be understood that tissue debris or soft tissue may be suctioned into the side apertures 640A, 640B when the negative pressure source 220 is operating and the ceramic cutter 620 is being rotated to cut tissue. In such cases, the scissor-like action between cutting edges 670 of the ceramic cutter 620 (FIGS. 15A and 15B) and sharp edges 662a, 662b will cut any tissue drawn into the apertures 640A and 640B. Similarly, if the probe is being used to coagulate or ablate tissue with the electrode 650 in a stationary position as shown in FIG. 14, then any tissue debris adhered to electrode 650 will be cut upon rotation of the ceramic cutting member 620 against the inner edges 662a and 662b of the side apertures 640A and 640B.

Figure 17:
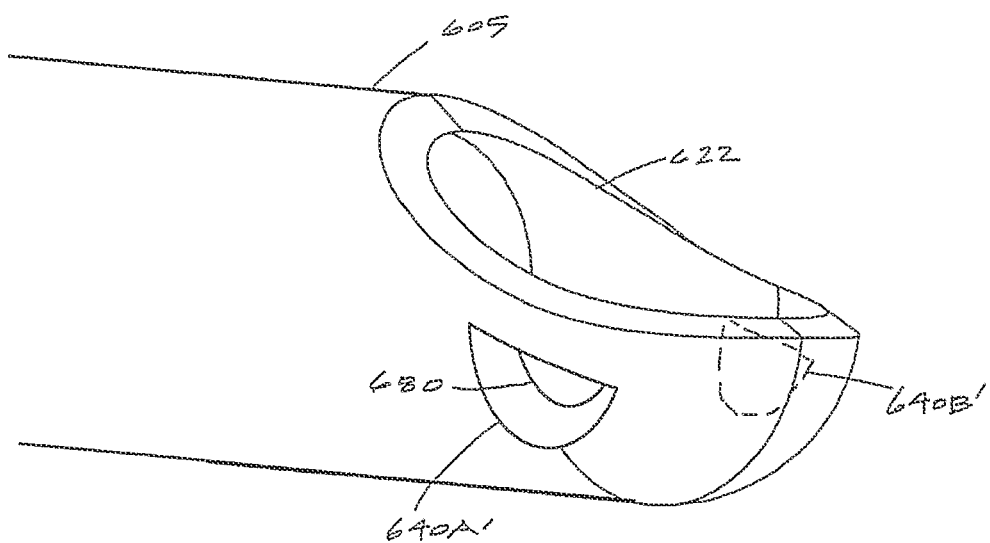
FIG. 17 is view of another outer sleeve similar to that of FIG. 14 with differently shaped side or cooling apertures.

FIG. 17 is view of another outer sleeve similar to that of FIG. 16 having differently shaped side apertures 640A' and 640B' with sharp inner edges 680.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A resecting probe, comprising:
    an outer sleeve with an open distal end and an axial bore that extends proximally from the open distal end through the outer sleeve, the outer sleeve including an outer cutting window in a side of the outer sleeve proximate the open distal end of the outer sleeve; and
    an inner sleeve rotatably received in the axial bore of the outer sleeve so that the inner sleeve can achieve at least a first rotational position and a second rotational position in the outer sleeve, the inner sleeve including an axial extraction channel that extends through the inner sleeve for connecting to a negative pressure source;
    a rotatable drive coupling fixed to a proximal portion of the inner sleeve and couplable to a motor shaft for rotating the inner sleeve in the outer sleeve;
    a ceramic cutting member disposed at a distal end of the inner sleeve for rotation with the inner sleeve, the ceramic cutting member including at least a first burr cutting edge formed therein, the ceramic cutting member also including an inner cutting window formed therein in a first side of the ceramic cutting member, wherein the ceramic cutting member being disposed at the distal end of the inner sleeve includes the inner cutting window communicating with the axial extraction channel in the inner sleeve; and
    an electrode carried on the ceramic cutting member on a second side of the ceramic cutting member opposite the first side,
    wherein, with the inner sleeve rotatably received in the axial bore of the outer sleeve and with the ceramic cutting member disposed at the distal end of the inner sleeve, part of the ceramic cutting member extends through the open distal end of the outer sleeve to position a proximal end of the first burr cutting edge and a proximal end of the electrode distally of the open distal end of the outer sleeve,
    wherein, in the first rotational position, the inner cutting window aligns sufficiently with the outer cutting window to allow fluid outflow to pass through the outer cutting window and into the axial extraction channel through the inner cutting window, and wherein, in the second rotational position, the electrode aligns with a longitudinal centerline of the outer cutting window.

2. The resecting probe of claim 1, wherein the ceramic cutting member includes at least a second burr cutting edge formed therein.

3. The resecting probe of claim 2, wherein the electrode is disposed circumferentially between the first burr cutting edge and the second burr cutting edge on the ceramic cutting member.

4. The resecting probe of claim 1, wherein a gap of less than 0.005 inches is maintained between the proximal end of the first burr cutting edge and the open distal end of the outer sleeve.

5. The resecting probe of claim 1, wherein a single opening in the outer sleeve provides the outer cutting window and the open distal end.

6. The resecting probe of claim 1, wherein a distal end of the inner cutting window is positioned proximally of the open distal end of the outer sleeve.

7. The resecting probe of claim 1, wherein a distal end of the inner cutting window is located proximally of the proximal end of the first burr cutting edge.

8. The resecting probe of claim 1, wherein the ceramic cutting member includes at least a first open slot formed therein in the second side of the ceramic cutting member proximal of the electrode.

9. The resecting probe of claim 1, wherein the inner sleeve includes an aspiration aperture therein that is adjacent the electrode.

10. The resecting probe of claim 1 in combination with a handpiece coupled to the resecting probe, the handpiece including a motor drive coupled to the rotatable drive coupling.

11. The resecting probe of claim 10 in combination with a controller coupled to the handpiece for controlling rotation of the motor drive and thereby controlling rotation of the inner sleeve in the outer sleeve.

12. The resecting probe of claim 11 in combination of a negative pressure source connected to the axial extraction channel.

13. The resecting probe of claim 12, wherein the outer sleeve further includes at least one flow aperture in a side wall of the outer sleeve and spaced apart from the outer cutting window.

14. The resecting probe of claim 13, wherein the at least one flow aperture comprises at least one elongated slot.

15. The resecting probe of claim 13, wherein the negative pressure source is controllable by the controller to draw fluid outflow through the at least one flow aperture and into the axial extraction channel in the inner sleeve when the inner sleeve is in the second rotational position.

16. The resecting probe of claim 15, wherein the negative pressure source is configured to draw fluid outflow through the at least one flow aperture at a rate of at least 25 ml/min.

17. The resecting probe of claim 15, wherein, in the first rotational position, the at least one flow aperture in the wall of the outer sleeve is blocked by a wall of the inner sleeve to inhibit passage of fluid outflow through the at least one flow aperture, and wherein, in the second rotational position, the at least one flow aperture in the wall of the outer sleeve is no longer blocked by the wall of the inner sleeve so that fluid outflow can pass through the at least one flow aperture and into the axial extraction channel in the inner sleeve.

18. The resecting probe of claim 17, wherein the inner sleeve includes an aspiration aperture therein that is adjacent the electrode.

19. The resecting probe of claim 18, wherein the aspiration aperture is open to the axial extraction channel so that, when the inner sleeve is in the second rotational position, the negative pressure source can simultaneously draw fluid outflow into the axial extraction channel through the aspiration aperture in the inner sleeve and through the at least one flow aperture in the outer sleeve.

20. The resecting probe of claim 19, wherein, when the inner sleeve is in the second rotational position, the negative pressure source is able to simultaneously draw fluid outflow through the aspiration aperture in the inner sleeve at a rate of between 10 ml/min and 50 ml/min and through the at least one flow aperture in the outer sleeve at a rate of at least 50 ml/min.

* * * * *